United States Patent [19]

Rossey et al.

[11] Patent Number: 4,794,185
[45] Date of Patent: Dec. 27, 1988

[54] PROCESS FOR THE PREPARATION OF IMIDAZOPYRIDINES

[75] Inventors: Guy Rossey; David Long, both of Montigny Le Bretonneux, Belgium

[73] Assignee: Synthelabo, France

[21] Appl. No.: 66,530

[22] Filed: Jun. 26, 1987

[30] Foreign Application Priority Data

Jun. 27, 1986 [FR] France .................. 86 09330

[51] Int. Cl.$^4$ .......................... C07D 471/04
[52] U.S. Cl. .................................. 546/121
[58] Field of Search ........................ 546/121

[56] References Cited

U.S. PATENT DOCUMENTS 4,382,938 5/1983 Kaplan et al. .................. 546/121
4,460,592 7/1984 Kaplan et al. .................. 546/121

OTHER PUBLICATIONS

Carelli et al., Chem. Soc. Perlin Trans. II, pp. 179–184 (1985).

*Primary Examiner*—Mary C. Lee
*Assistant Examiner*—Bernard I. Dentz
*Attorney, Agent, or Firm*—Wegner & Bretschneider

[57] ABSTRACT

A process for the preparation of an imidazopyridine which is a compound of formula (I)

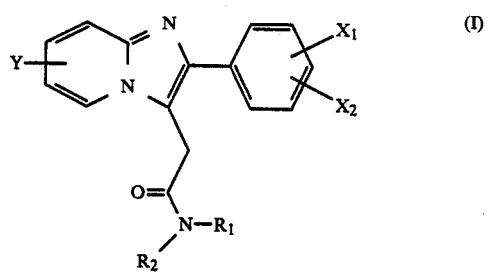

in which:
- Y denotes hydrogen, a halogen or a $C_{1-4}$ alkyl group;
- $X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group; and
- $R_1$ and $R_2$ denote, independently of each other, hydrogen or a $C_{1-5}$ alkyl group, with the proviso that $R_1$ and $R_2$ do not both denote hydrogen, or a salt thereof;

which process comprises reacting a compound of formula (V)

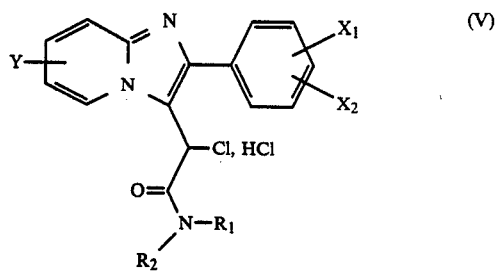

wherein Y, $X_1$, $X_2$, $R_1$ and $R_2$ are as defined above, with a reducing agent and if desired converting the resulting compound of formula (I) into a salt, together with intermediates of formulae:

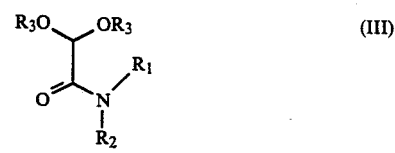

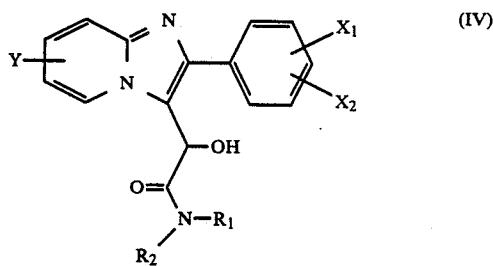

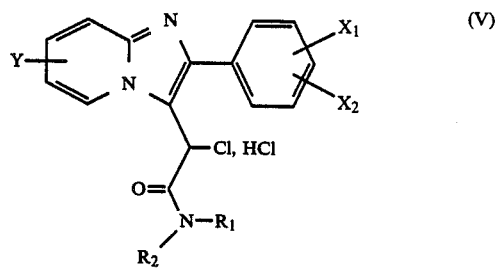

The final products have useful pharmacological properties, e.g. as anxiolytics.

2 Claims, No Drawings

PROCESS FOR THE PREPARATION OF IMIDAZOPYRIDINES

The present invention relates to a process for the preparation of imidazopyridines and to intermediates useful in the process and to a process for the preparation of some of these intermediates.

These compounds and their uses are described in European Pat. No. 0,050,563.

The present invention therefore provides a process for the preparation of an imidazopyridine which is a compound of formula (I)

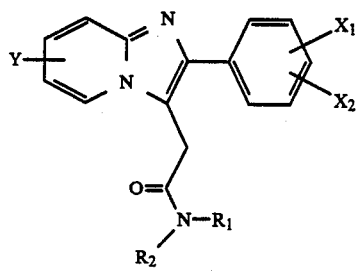

in which:

Y denotes hydrogen, a halogen or a $C_{1-4}$ alkyl group;

$X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group; and $R_1$ and $R_2$ denote, independently of each other, hydrogen or a $C_{1-5}$ alkyl group, with the proviso that $R_1$ and $R_2$ do not both denote hydrogen, or a salt thereof;

which process comprises reacting a compound of formula (V)

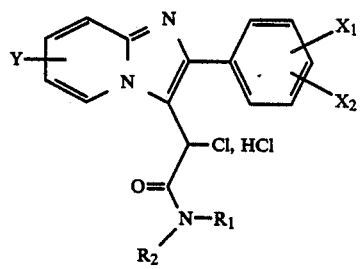

wherein Y, $X_1$, $X_2$, $R_1$ and $R_2$ are as defined above, with a reducing agent, and if desired converting the resulting compound of formula (I) into a salt.

The compound of formula (V) may, for example, be prepared by first reacting an imidazopyridine of formula (II) with a compound of formula (III) as shown in the appendix wherein Y, $X_1$, $X_2$, $R_1$ and $R_2$ are as defined above and $R_3$ denotes a $C_{1-4}$ alkyl group at a temperature of 20° to 100° C. in the presence of an acid and in a solvent, for example a chlorinated solvent such as dichloroethane or dichloromethane, or in an acid such as formic, propionic or butyric acid, preferably acetic acid, reacting the compound of formula (IV) obtained as shown in the appendix with a compound releasing chlorine, such as thionyl chloride, phosphoryl chloride, phosgene or oxalyl chloride, in a solvent, e.g., a chlorinated solvent such as dichloromethane or dichloroethane.

The reducing agent may be, for example, $NaBH_4$, $Zn(BH_4)_2$, $KBH_4$, $LiBH_4$, a dithionite or a derivative of any one of these or a mixture of Zn and HCl.

The compound of formula (I) may be converted into a salt by any normal means.

The process of the invention enables the compounds of formula (I) to be obtained in an excellent yield, for example from 50 to 95%, and the compounds to be obtained in excellent purity, after working up.

The compounds of formulae (II), (IV) and (V) as defined above also form part of the invention.

The starting compounds of formula (II) are described in the literature.

The compounds of formula (III) as defined above may, for example, be prepared by reacting a compound of formula

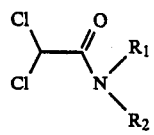

in which $R_1$ and $R_2$ are as defined above with a source of alkoxide or alkanolate ions, for example an alkali metal alkoxide, especially sodium alkoxide or an alkanol in acetonitrile.

All of the alkyl or alkoxy moieties referred to above may be straight- or branched-chained.

The following examples further illustrate the present invention.

EXAMPLE 1

Preparation of the starting compound (III): N,N-dimethyl-2,2-dimethoxyacetamide

1.1. N,N-dimethyl-2,2-dichloroacetamide 550 ml (5 moles) of 40% dimethylamine in water are introduced into a jacketed reactor and then the jacket is cooled to approximately −10° C. 192.4 ml (2 moles) of 2,2-dichloroacetyl chloride are then added dropwise over 4 h. The reaction temperature is controlled between −10° and 0° C. When the reaction is finished the product, which is denser than water, is allowed to separate in the reactor. This product is recovered and the aqueous phase is extracted with dichloromethane. The organic phases are mixed. They are washed to remove acid.

B.p.: 109° C. at 15 mmHg.

1.2. N,N-dimethyl-2,2-dimethoxyacetamide.

73.6 g of the compound obtained earlier are introduced into a 500-ml round flask and 150 ml of acetonitrile ($CH_3CH$) are added. 180 ml (2 equivalents) of 29% strength sodium methylate in methanol are then added fairly quickly. These are heated to reflux temperature for 3 h. They are allowed to cool. The sodium chloride is filtered off, the solvents are evaporated off and the residue is taken up (3 times) with 50 ml of tert-butyl methyl ether (TBME) to remove the remaining sodium chloride. The mixture is taken up with 100 ml of water and allowed to separate. The aqueous phase is evaporated to dryness and then taken up with TBME, and the sodium chloride is filtered off. The organic phases are combined together and the solvents are then evaporated off. The product is then obtained.

B.p.=101° C. (15 mmHg).

EXAMPLE 2

N,N-di-n-propyl-2,2-dimethoxyacetamide 2.1. N,N-di-n-propyl-2,2-dichloroacetamide.

60 g of dipropylamine are reacted with 40.4 g of dichloroacetyl chloride in 100 ml of dichloromethane at 0° C. in a 500-ml conical flask. The yellow solution is washed with 200 ml of water, dried and concentrated. An oil which crystallizes is obtained.

M.p.=53° C.

2.2. N,N-di-n-propyl-2,2-dimethoxy acetamide 160 g of sodium methylate are reacted with 66.4 g of the compound obtained above in 300 ml of acetonitrile at 80° C. for 50 minutes. The reaction mixture is cooled and acidified with HCl, the salts are filtered off and, after being concentrated, the residue is taken up with 300 ml of dichloromethane. The organic phase is washed with water, dried and concentrated. An oil is obtained.

B.p.=140° C. (15 mmHg).

EXAMPLE 3

6-Methyl-N,N-dimethyl-2(4-methylphenyl)imidazo[1,2-a]pyridine-3-acetamide 3.1. 6-Methyl-N,N-dimethyl-2-(4-methylphenyl)-α-hydroxyimidazo[1,2-a]pyridine-3-acetamide (compound IV).

93 g of compound (III) in which $R_1$, $R_2$ et $R_3$ each denote the methyl radical, 15.8 ml of water, 64.8 ml of concentrated acetic acid and 15.8 ml of 37% strength hydrochloric acid are introduced into a 2-liter reactor equipped for azeotropic distillation. The mixture is heated to about 43°–46° C. for 50 min.

The pH is then adjusted to 4–5 with 17 g of sodium acetate and 850 ml of 1,2-dichloroethane and 100 g of 6-methyl-2-(4-methylphenyl)imidazo[1,2-a]pyridine are added. The mixture is then heated to reflux for 2 hours. Approximately 20 ml of water are removed as an azeotrope during this time (azeotropy temperature: 78° C.).

The temperature is returned to 73° C. and 250 ml of a saturated sodium bicarbonate solution are added dropwise, followed by 35 ml of sodium hydroxide solution so as to adjust the pH to 7.

The solvent is then removed by distillation and, after cooling to 55° C., the last traces of 1,2-dichloroethane are removed under vacuum.

55 ml of water and 250 ml of isopropanol are added, followed by sodium hydroxide solution to give a pH of 10, which causes the product to crystallize in the form of a white solid.

The product is filtered off, washed with water and dried under vacuum in the presence of $P_2O_5$ for 6 h.

The yield is 89%.

M.p.=174°–176° C.

3.2. 6-Methyl-N,N-dimethyl-2-(4-methylphenyl)-α-chloroimidazo[1,2-a]pyridine-3-acetamide hydrochloride (compound V).

40 g of the compound (IV) obtained earlier and 180 ml of 1,2-dichloroethane are introduced into a 0.5-l reactor.

The mixture is heated to 50° C. and a solution of 11.2 ml of thionyl chloride in 30 ml of 1,2-dichloroethane is added dropwise over 1 h.

The temperature rises to 60° C.

The mixture is then heated to reflux for 1 h 30 min, is cooled to about 40°–50° C. and part of the 1,2-dichloroethane is evaporated off under vacuum to strip off excess $SOCl_2$.

200 ml of isopropyl ether are then added and the mixture is cooled to 10° C. and then stirred for 1 h 30 min.

The solid is rinsed with 100 ml of isopropyl ether and is dried under vacuum in an oven at 50°–60° C. for 6 h.

The yield is 97.6%.

M.p.=186° C. (dec).

3.3. 6-Methyl-N,N-dimethyl-2-(4-methylphenyl)imidazo[1,2-a]pyridine-3-acetamide and its hemitartrate (compound I).

3.3.1. 50 g of the hydrochloride obtained under 2 are dissolved in 250 ml of methanol in a 1-liter reactor.

A solution of 20 g of sodium borohydride in 150 ml of water is then added quickly over 2–3 min.

The stirring is continued for 1 h 30 min.

150 ml of a saturated sodium carbonate solution and 250 ml of water are then added in order to complete the precipitation.

The light-brown precipitate is filtered off, washed copiously with water and dried in an oven for 18 h.

The yield is 62%.

M.p.=194°–196° C.

3.3.2. 25 g of the compound (I) are dissolved in 180 ml of methanol.

A solution of 6.1 g of L(+)-tartaric acid in 60 ml of methanol is then added.

Crystallization is allowed to take place.

The yield is 94%. M.p.=197° C.

EXAMPLE 4

N,N-di-n-propyl-6-chloro-2-(4-chlorophenyl)imidazo[1,2-a]pyridine-3-acetamide 4.1. N,N-di-n-propyl-6-chloro-2-(4-chlorophenyl)-α-hydroxyimidazol[1,2-a]pyridine-3-acetamide.

A mixture of 56.5 ml (0.226 mole) of compound (III) in which $R_1$ and $R_2$ are n-propyl radicals and $R_3$ is the methyl radical, 67 ml of water, 28 ml of acetic acid and 67 ml of concentrated (12N) hydrochloric acid is stirred at 50° C. for 20 min. 83.3 g (1 mole) of sodium acetate are then added and stirred for 30 min. 50 g (0.19 mole) of 6-chloro-2-(4-chlorophenyl)-imidazo[1,2-a]pyridine are then added and the reaction mixture is stirred at 90° C. for 2 h.

After cooling to 20° C., the product is precipitated at pH 10 by adding approximately 100 ml of 10N sodium hydroxide solution after 16 h of stirring at ambient temperature. The precipitate is filtered off, washed 4 times with 100 ml of water and dried in a vacuum oven (70° C., 20 mbar). The yield is 93.8%. M.p.=133° C.

4.2. 6-Chloro-N,N-di-n-propyl-2-(4-chlorophenyl)-α-chloroimidazo[1,2-a)]pyridine-3-acetamide hydrochloride.

A suspension of 100 g (0.237 mole) of the compound obtained earlier in 340 ml of 1,2-dichloroethane is added to a solution of 21.6 ml (0.3 mole) of thionyl chloride in 100 ml of 1,2-dichloroethane.

The mixture is stirred for 16 h at ambient temperature. It is then heated and kept at a temperature of 70° C., for 1 h until gas evolution ceases. 140 ml of solvent are then removed under reduced pressure.

While cooling to 10° C., 340 ml of diisopropyl ether are added to complete the precipitation. After one hour's stirring at this temperature, the precipitate is filtered off, washed twice with 100 ml of diisopropyl ether and is dried under vacuum (60° C., 10 mbar) for 8 h. The yield is 95%. M.p.=190° C. (dec).

4.3. N,N-di-n-propyl-6-chloro-2-(4-chlorophenyl)imidazo[1,2-a]pyridine-3-acetamide.

A solution of 17 g (0.37 mole) of sodium borohydride (NaBH$_4$) in 400 ml of water is added over 22 min to a suspension of 50 g (0.105 mole) of the compound obtained earlier in 300 ml of isopropanol, while the temperature is maintained in the neighbourhood of 20° C. by circulating glycol at −5° C. through the reactor jacket. After 1 h of stirring, 300 ml of water are added, stirring is again applied for 1 h and the solid is filtered off and washed 8 times with 150 ml of water and 3 times with 70 ml of diisopropyl ether, and is dried in an oven for 8 h (60° C., 10 mbar). The yield is 50%.

M.p.=138°–139° C. (B polymorph).

Other compounds (I) may be prepared according to the same reaction scheme.

The compounds (III), (IV) and (V), prepared by way of examples, are shown in the following tables:

TABLE (I)

(III)

| Compound | $R_1$ | $R_2$ | $R_3$ | B.p. (°C.) |
|---|---|---|---|---|
| 1 | CH$_3$ | CH$_3$ | CH$_3$ | 101 (15 mmHg) |
| 2 | n-C$_3$H$_7$ | n-C$_3$H$_7$ | CH$_3$ | 140 (15 mmHg) |
| 3 | CH$_3$ | CH$_3$ | C$_2$H$_5$ | 105 (14 mmHg) |
| 4 | n-C$_3$H$_7$ | n-C$_3$H$_7$ | C$_2$H$_5$ | 135 (13 mmHg) |

TABLE (II)

(IV)

| Compound | Y | $X_1$ | $X_2$ | $R_1$ | $R_2$ | M.p. (°C.) |
|---|---|---|---|---|---|---|
| 1 | 6-CH$_3$ | 4-Cl | H | CH$_3$ | CH$_3$ | 234 |
| 2 | 6-Cl | 4-Cl | H | n-C$_3$H$_7$ | n-C$_3$H$_7$ | 130–132 |
| 3 | 8-CH$_3$ | 4-Cl | H | CH$_3$ | CH$_3$ | 191–192 |
| 4 | 6-CH$_3$ | 4-CH$_3$ | H | CH$_3$ | CH$_3$ | 174–175 |
| 5 | 6-CH$_3$ | 3-CH$_3$ | H | CH$_3$ | CH$_3$ | 191–192 |

TABLE (III)

(V)

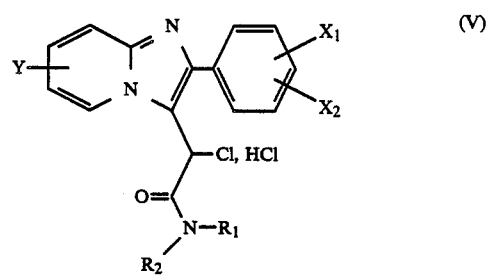

TABLE (III)-continued (V)

| Compound | Y | $X_1$ | $X_2$ | $R_1$ | $R_2$ | M.p. (°C.) |
|---|---|---|---|---|---|---|
| 1 | 6-CH$_3$ | 4-CH$_3$ | H | CH$_3$ | CH$_3$ | 186 (dec) |
| 2 | 6-Cl | 4-Cl | H | n-C$_3$H$_7$ | n-C$_3$H$_7$ | 190 (dec) |

APPENDIX
Reaction scheme

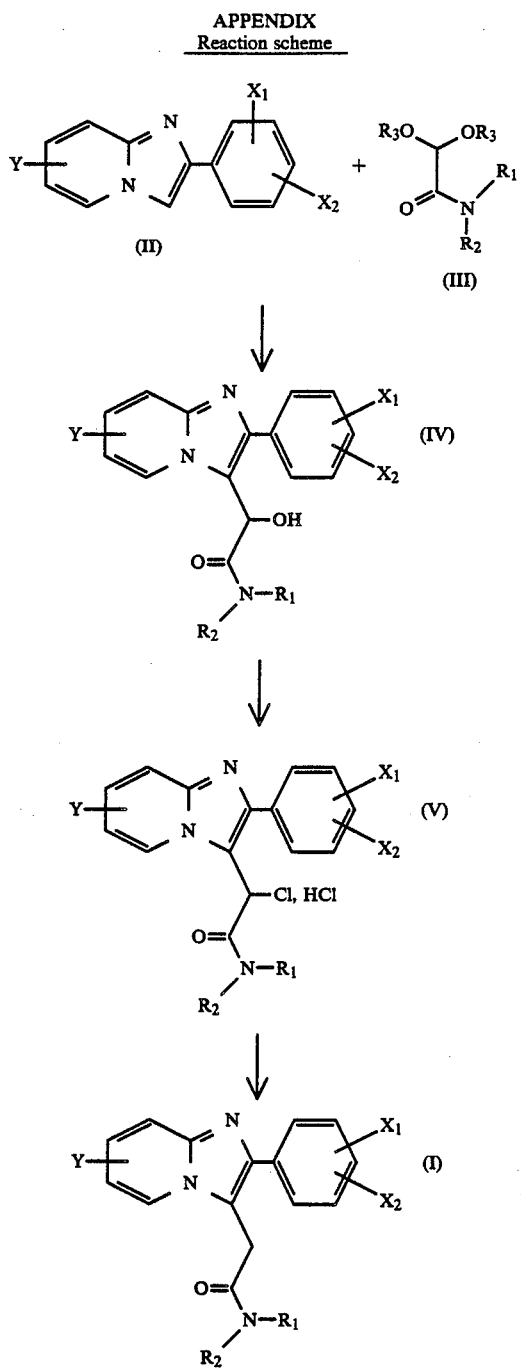

We claim:

1. A process for the preparation of an imidazopyridine which is a compound of formula (I)

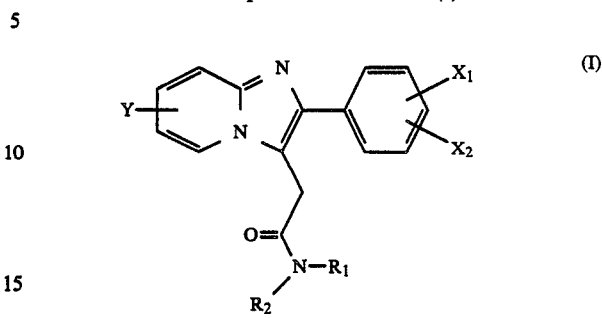

in which:
- Y denotes hydrogen, a halogen or a $C_{1-4}$ alkyl group;
- $X_1$ and $X_2$ denote, independently of each other, hydrogen, a halogen or a $C_{1-4}$ alkoxy, $C_{1-6}$ alkyl, $CF_3$, $CH_3S$, $CH_3SO_2$ or $NO_2$ group; and
- $R_1$ and $R_2$ denote, independently of each other, hydrogen or a $C_{1-5}$ alkyl group, with the proviso that $R_1$ and $R_2$ do not both denote hydrogen,
- or a salt thereof;

which process comprises reacting a compound of formula (V)

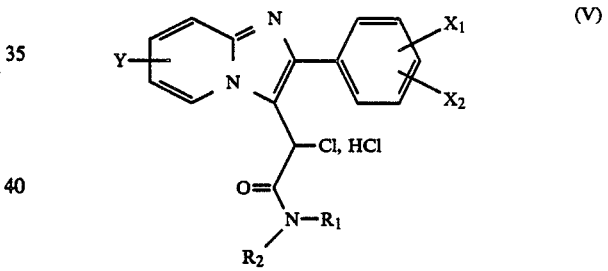

wherein Y, $X_1$, $X_2$, $R_1$ and $R_2$ are as defined above, with a reducing agent and if desired converting the resulting compound of formula (I) into a salt.

2. A process according to claim 1 wherein the reducing agent is $NaBH_4$, $KBH_4$, $LiBH_4$, $Zn(BH_4)_2$, a dithionite, a derivative of any one of these or a mixture of Zn and HCl.

* * * * *